United States Patent [19]
Sage et al.

[11] Patent Number: 6,074,369
[45] Date of Patent: Jun. 13, 2000

[54] LOW-PROFILE AUTOMATIC INJECTION DEVICE WITH SELF-EMPTYING RESERVOIR

[75] Inventors: Burton H. Sage, Raleigh; Robert I. Connelly, Durham, both of N.C.

[73] Assignee: Becton, Dickinson and Company, Franklin Lakes, N.J.

[21] Appl. No.: 09/306,904

[22] Filed: May 7, 1999

Related U.S. Application Data

[63] Continuation of application No. 09/027,291, Feb. 20, 1998, Pat. No. 5,957,895.

[51] Int. Cl.[7] .................................................. A61M 5/178
[52] U.S. Cl. ........................... 604/181; 604/131; 604/132
[58] Field of Search .................................... 604/181, 131, 604/132, 133, 134, 183–185

[56] References Cited

U.S. PATENT DOCUMENTS

| | | |
|---|---|---|
| 4,196,732 | 4/1980 | Wardlaw . |
| 4,772,263 | 9/1988 | Dorman et al. . |
| 4,781,688 | 11/1988 | Thoma et al. . |
| 5,011,477 | 4/1991 | Winchell et al. . |
| 5,045,064 | 9/1991 | Idriss . |
| 5,649,910 | 7/1997 | Kriesel et al. . |
| 5,693,018 | 12/1997 | Kriesel et al. . |
| 5,716,343 | 2/1998 | Kriesel et al. . |
| 5,957,895 | 9/1999 | Sage et al. .............................. 604/181 |

*Primary Examiner*—John D. Yasko
*Attorney, Agent, or Firm*—Donna R. Fugit

[57] ABSTRACT

A device for delivering a liquid therapeutic preparation into the body of a patient by injection into or through the skin of the patient comprises a low-profile housing having a bottom surface adapted to be brought into contact with the skin of the patient. A reservoir is disposed within the housing for containing a liquid therapeutic preparation to be administered. An injection needle is disposed generally horizontally in the housing, and is adapted to communicate with the reservoir. The injection needle has a bent injection end which is adapted to project through a needle aperture in the bottom surface of the housing. A movable needle carrier is disposed in the housing for carrying the injection needle and for causing the injection end of the needle to project through the needle aperture upon movement of the needle carrier. The needle carrier and the injection needle are disposed in a side-by-side relationship with the reservoir in the housing in order to minimize the height of the housing above the bottom surface. As a result, the housing is sufficiently low in height to allow the device to be worn inconspicuously under the clothing of the patient.

16 Claims, 13 Drawing Sheets

LOW-PROFILE AUTOMATIC INJECTION DEVICE WITH SELF-EMPTYING RESERVOIR

This is a continuation of U.S. Ser. No. 09/027,291, filed Feb. 20, 1998 now U.S. Pat. No. 5,957,895.

BACKGROUND OF THE INVENTION

The present invention relates generally to a device for delivering a liquid therapeutic preparation into the body of a patient by injection into or though the patient's skin. More particularly, the invention relates to a low-profile automatic injection device that can be worn inconspicuously under the clothing of a patient to allow a liquid therapeutic preparation (such as insulin) to be administered over an extended period of time, and that incorporates a self-emptying reservoir to eliminate the need for a pump or other type of discharge device.

Various types of automatic injection devices have been developed to allow drug solutions and other liquid therapeutic preparations to be administered by untrained personnel. Generally, these devices include a reservoir that is pre-filled with the liquid therapeutic preparation, and some type of automatic needle-driving mechanism (usually of the spring-loaded type) that can be triggered by the user. Examples of such devices may be found in U.S. Pat. Nos. 4,188,950, 4,196,732, 4,258,713, 4,227,528 and 4,378,015, all to Stephen C. Wardlaw. Still further examples can be found in U.S. Pat. No. 4,214,584 to Smirnov et al., U.S. Pat. Nos. 4,894,054 and 5,527,287, both to Miskinyar, and U.S. Pat. No. 5,616,132, to Newman.

In order to start the flow of the liquid therapeutic preparation when the needle is injected, the devices disclosed in the aforementioned patents generally employ movable ampoules, pistons or other complex arrangements which are somewhat difficult to manufacture. Moreover, the design of these devices generally requires that the reservoir be positioned above the needle driving mechanism, which results in a device of considerable height. This is not necessarily a problem when the drug solution is to be injected as a bolus at one discrete time, as most of these devices are designed to do, but it is a distinct disadvantage when the drug solution is to be infused into the patient over an extended period of time. In these latter instances, the injection device may have to be held in contact with the patient's skin (e.g., by tape or an adhesive) for several hours or more, and this is difficult to achieve when the device has a large height dimension.

Another class of devices includes those which are capable of gradually infusing a liquid therapeutic preparation into the skin of a patient. In some cases, these devices are small enough (both in height and in overall size) to allow them to be "worn" by an ambulatory patient while the liquid therapeutic preparation is being infused into the patient. Examples of devices which fall in to this class include those disclosed in U.S. Pat. Nos. 4,340,048 and 4,753,651, both to Eckenhoff, U.S. Pat. No. 4,734,092, to Millerd, U.S. Pat. No. 4,781,688, to Thoma et al., U.S. Pat. No. 4,886,499, to Cirelli et al., U.S. Pat. No. 5,656,032, to Kriesel et al., and PCT Publication Nos. WO 95/13838 and WO 97/21457, both to Elan Medical Technologies, Ltd.

Unfortunately, most of the automatic infusion devices disclosed in the prior art are fairly complex in design and, as a result, cannot be made as small and inexpensive as might be desired. Generally, the complexity of these devices results from three factors. One factor is the need for a pump or other type of discharge mechanism to force the liquid therapeutic preparation to flow out of the reservoir and into the injection or infusion needle. Another factor is the need for some type of valve or flow control mechanism to cause the liquid therapeutic preparation to begin to flow at the proper time. A third factor, which applies to those devices that are designed to inject the infusion needle into the patient automatically, is the need for a suitable injection mechanism that can be triggered by the user. The structures required to perform these functions add size and complexity to the infusion device, making it larger than desired and relatively expensive to manufacture.

Accordingly, a need exists for an automatic injection device that is small and has a low-profile configuration, allowing it to be conveniently handled and worn (preferably in an inconspicuous manner under the clothing) by an ambulatory patient. A need also exists for an automatic injection device which is capable of infusing a drug solution or other liquid therapeutic preparation into the skin of a patient over an extended period of time. Finally, a need exists for an automatic injection device whose basic design allows it to be not only small and low in height, but also simple and inexpensive to manufacture.

SUMMARY OF THE INVENTION

In accordance with one aspect of the present invention, a device is provided for delivering a liquid therapeutic preparation into the body of a patient by injection into or through the skin of the patient. The device comprises a housing having a bottom surface adapted to be brought into contact with the skin of a patient, with the bottom surface of the housing having a needle aperture therein. A reservoir is disposed within the housing for containing a liquid therapeutic preparation to be administered to the patient. A needle carrier is also disposed within the housing and is movable between first and second positions within the housing, such movement occurring in a horizontal direction that is generally parallel to the bottom surface of the housing. An injection needle is carried by the needle carrier for movement therewith. The injection needle has a first portion extending generally perpendicular to the bottom surface of the housing for penetrating the skin of the patient, and a second portion extending generally parallel to the bottom surface of the housing for communicating with the reservoir. In the first position of the needle carrier, the first portion of the injection needle is retracted within the housing and the second portion of the injection needle does not communicate with the reservoir. In the second position of the needle carrier, the first portion of the injection needle projects through the needle aperture and the second portion of the injection needle communicates with the reservoir. In this way, movement of the needle carrier between the first and second positions causes the injection needle to penetrate the skin of the patient, and also causes the liquid therapeutic preparation to begin to flow through the injection needle into the body of the patient.

In accordance with a further aspect of the present invention, a device for delivering a liquid therapeutic preparation into the body of a patient by injection into or through the skin of the patient comprises a low-profile housing having a bottom surface adapted to be brought into contact with the skin of the patient. The bottom surface of the housing has a needle aperture therein, and the housing is sufficiently low in height to allow the device to be worn inconspicuously under the clothing of the patient. A reservoir is disposed within the housing for containing a liquid therapeutic preparation to be administered. An injection needle is disposed generally horizontally in the housing, and is adapted to communicate with the reservoir. The injection needle has a bent injection end which is adapted to project through the needle aperture. A movable needle carrier is disposed in the housing for carrying the injection needle and for causing the injection end of the needle to project through the needle aperture upon movement of the needle carrier. The needle carrier and the injection needle are disposed in a side-by-side relationship with the reservoir in the housing in order to minimize the height of the housing above the bottom surface.

In accordance with a still further aspect of the present invention, a device for delivering a liquid therapeutic preparation into the body of a patient by injection into or through the skin of the patient comprises a housing adapted to be held in contact with the patient's skin. A reservoir is disposed within the housing for containing a liquid therapeutic preparation to be administered. The reservoir includes a Belleville spring which exerts pressure on the liquid therapeutic preparation to discharge the liquid therapeutic preparation from the reservoir at a relatively constant rate. An injection needle is adapted to communicate with the reservoir and to project from the housing in order to inject the liquid therapeutic preparation into or through the skin of the patient.

BRIEF DESCRIPTION OF THE DRAWINGS

The various objects, advantages and novel features of the present invention will be more readily appreciated from the following detailed description when read in conjunction with the appended drawings, in which.

Throughout the drawings, like reference numerals will be understood to refer to like parts and components.

DETAILED DESCRIPTION OF THE PREFERRED EMBODIMENTS

Figure 1:
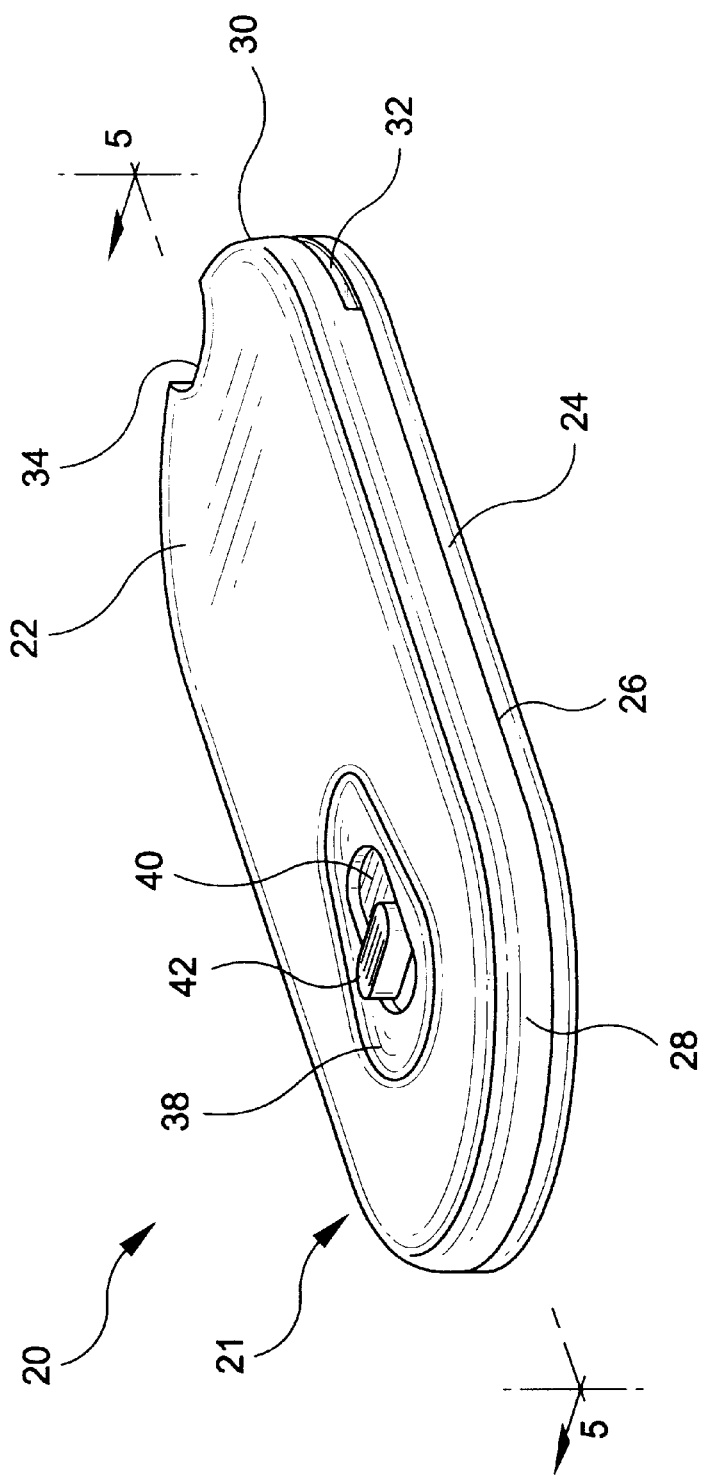
FIG. 1 is a top perspective view of an automatic injection device constructed in accordance with a first embodiment of the present invention.
Figure 2:
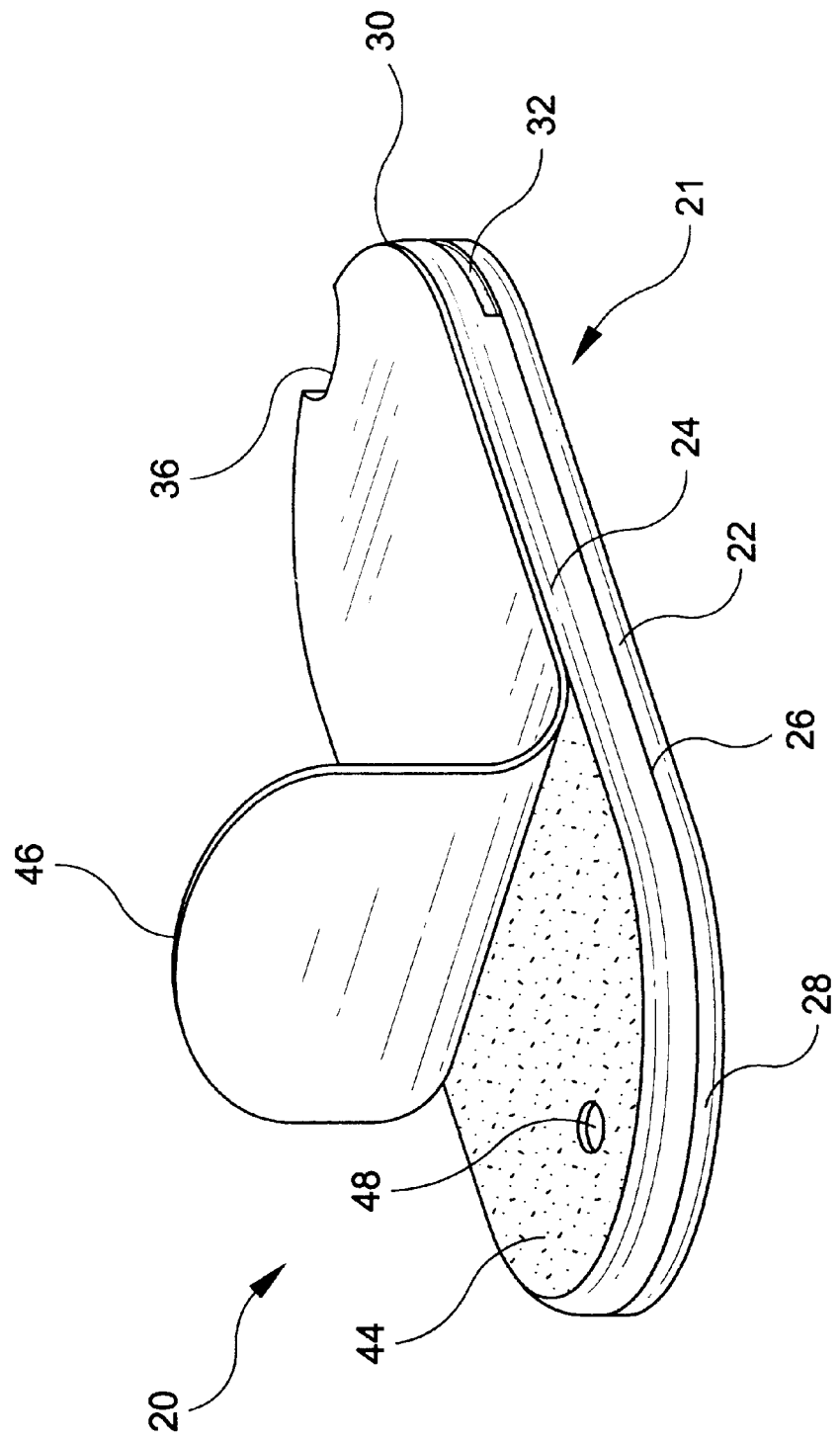
FIG. 2 is a bottom perspective view of the automatic injection device of FIG. 1, illustrating the needle aperture and peelable release liner thereof.

An automatic injection device 20 constructed in accordance with a first embodiment of the present invention is illustrated generally in the top and bottom perspective views of FIGS. 1 and 2, respectively. The device 20 includes a rigid external housing 21 that consists of an upper housing portion 22 and a lower housing portion 24. The housing portions 22 and 24 may be made of a suitable plastic material, such as polycarbonate, and are joined to each other along a horizontal seam 26. The plastic material used for the housing 21 is preferably opaque, but may be transparent or translucent if desired. When viewed from above or below, the housing 21 has an oblong shape with rounded ends, as shown. The forward end 28 of the housing 21 is closed, but the rear end 30 of the housing includes a horizontally-extending slot 32 (formed by a notch in the upper housing portion 22) which allows access to the interior of the housing. The slot 32 allows a pre-filled liquid reservoir or dose chamber to be installed in the housing 21 after the device 20 has been assembled. Horizontal, crescent-shaped cut-outs 34 and 36 are formed in the upper and lower portions 22 and 24 of the housing 21 at the rear end 30 thereof to allow the liquid reservoir to be fully inserted.

As shown in FIG. 1, the upper portion 22 of the housing is formed with a recessed area 38 in which a hole 40 is formed. The hole 40 is elongated in the lengthwise direction of the device 20, and accommodates a slide button 42 which is operated by the user. The top surface of the slide button 42 is ribbed in a direction perpendicular to the direction of button movement, as shown, to allow the user's finger to engage the button 42 without slipping. The button 42 is initially in the position shown in FIG. 1 and is moved rearwardly (i.e., in the direction toward the rear end 30 of the housing 21) by the user during operation of the device 20. As will be described in detail below, movement of the button 42 causes an injection needle to project from the bottom of the housing 21 and also causes the liquid therapeutic preparation to begin to flow through the injection needle from the internal reservoir.

As shown in FIG. 2, the bottom surface of the housing is flat and carries a layer of pressure-sensitive adhesive 44 which allows the device 20 to be affixed to the skin of a patient. The tackiness of the adhesive layer 44 is sufficient to allow the device 20 to remain securely attached to the patient's body, but is weak enough to allow the device 20 to be removed from the skin after use without discomfort. A suitable adhesive which may be used for this purpose is available from 3M Company of St. Paul, Minn. Preferably, the bottom surface of the housing 21 is roughened or textured to allow for better adhesion of the pressure-sensitive adhesive layer 44 to the plastic material of the housing. A release liner 46, made of coated paper or a thin sheet of plastic, covers the adhesive layer 44 prior to use of the device 20. When the release liner 46 is removed, it uncovers not only the adhesive layer 44 but also a small round hole 48 that is formed through the bottom portion 24 of the housing near its forward end 28. The hole 48 serves as a needle aperture for allowing an injection needle to protrude from the bottom of the device 20 when the slide button 42 of FIG. 1 is actuated, as will be described in detail below.

In the preferred embodiment, the automatic injection device 20 of FIGS. 1 and 2 is approximately 3.6 inches in length, approximately 1.8 inches in width and approximately 0.4 inch or less in height. However, these dimensions are given merely by way of example and not by way of limitation, it being understood that both the dimensions of the device 20 and its overall shape or geometry may be varied in order to suit the requirements of particular applications.

Figure 3:
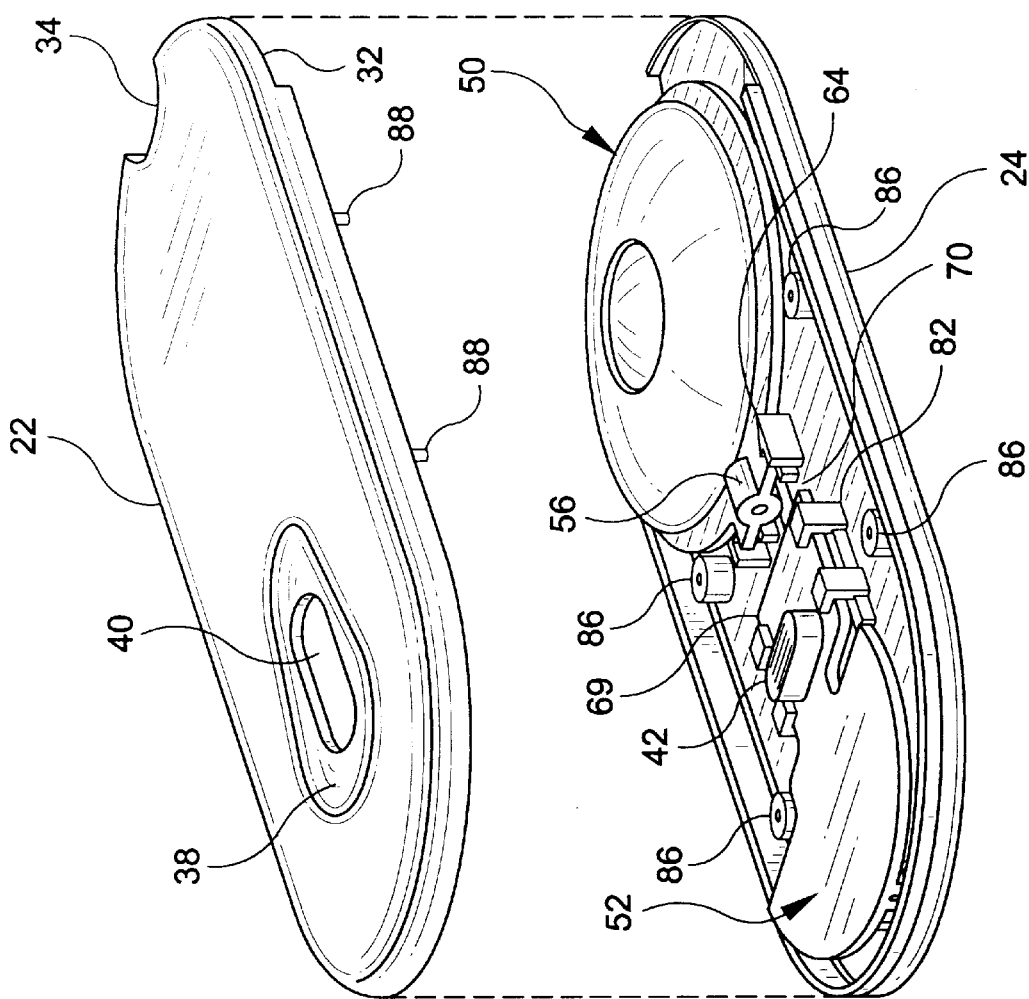
FIG. 3 is a partially exploded perspective view of the automatic injection device of FIGS. 1 and 2, with the top portion of the housing removed and the internal components of the device shown in their operative positions in the bottom portion of the housing.
Figure 4:
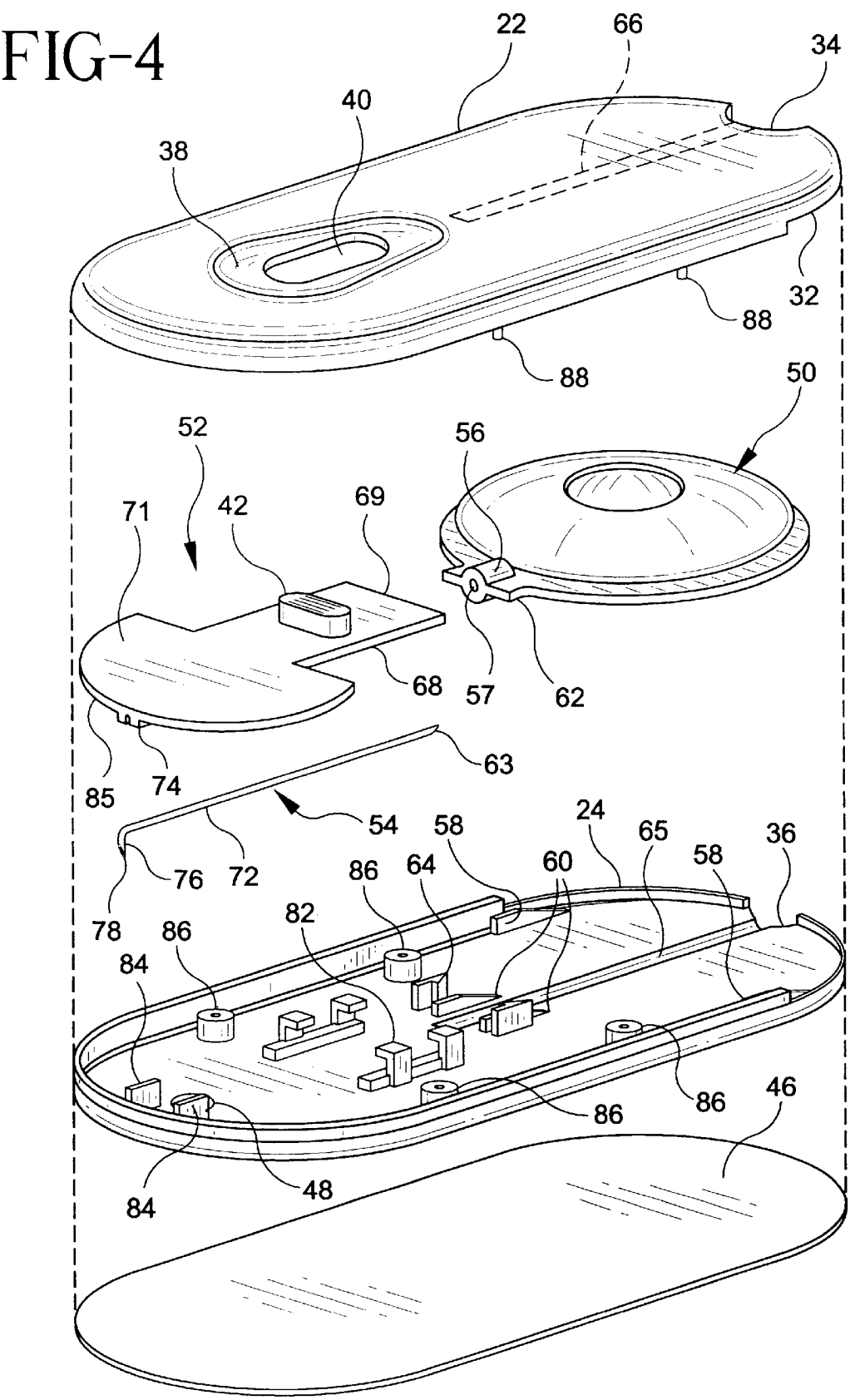
FIG. 4 is a fully exploded perspective view of the automatic injection device of FIGS. 1–3, with the internal components of the device shown removed from the bottom portion of the housing.
Figure 9:
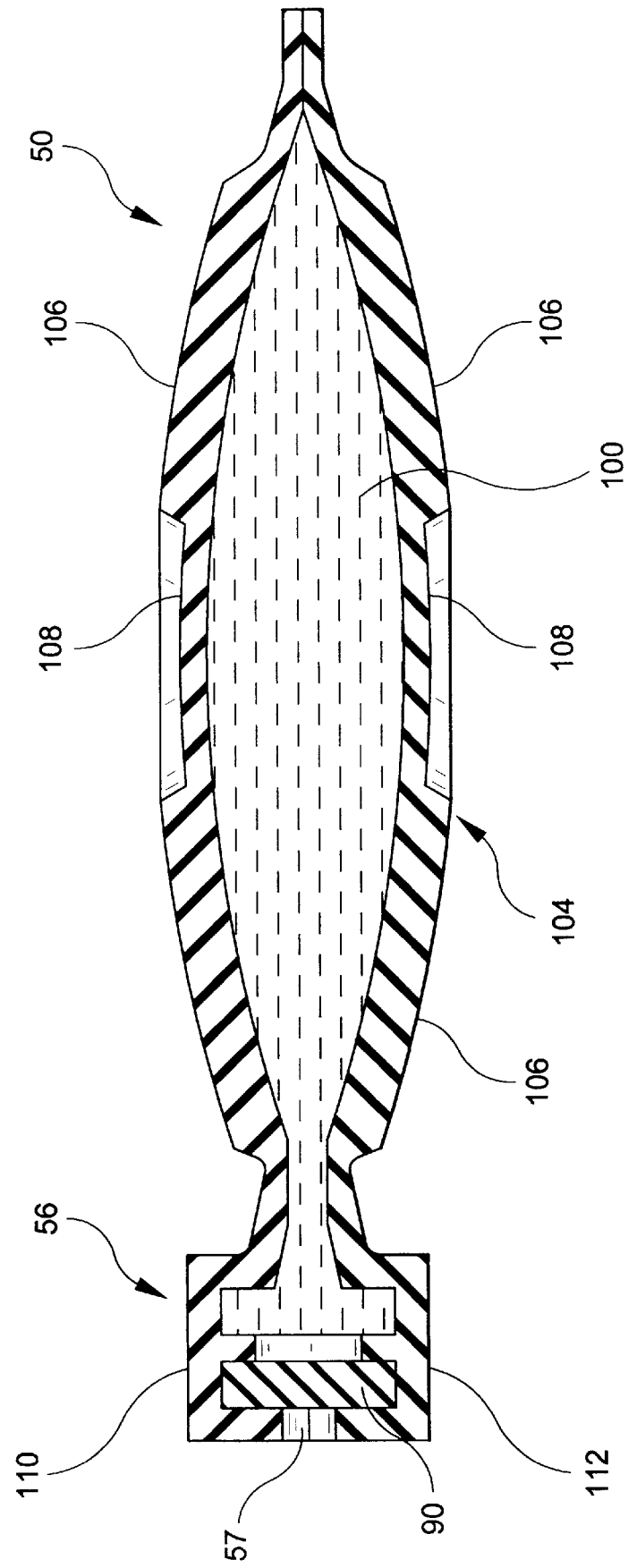
FIG. 9 is a cross-sectional view of the liquid reservoir or dose chamber used in the device of FIGS. 1–8, with the liquid therapeutic preparation present within the reservoir.
Figure 10:
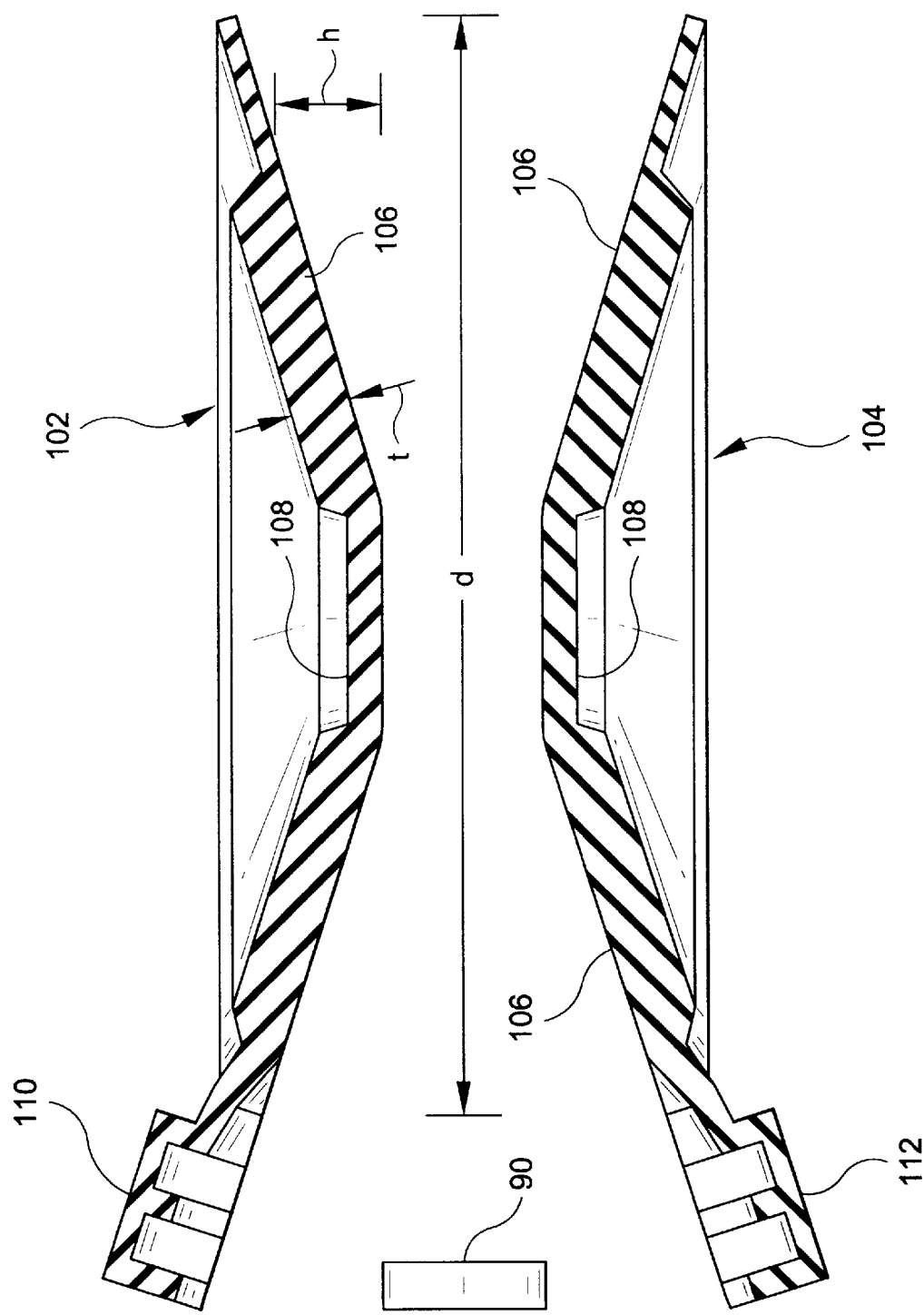
FIGS. 10 and 11 illustrate the components of the liquid reservoir of FIG. 8 and the manner in which they are assembled.
Figure 11:
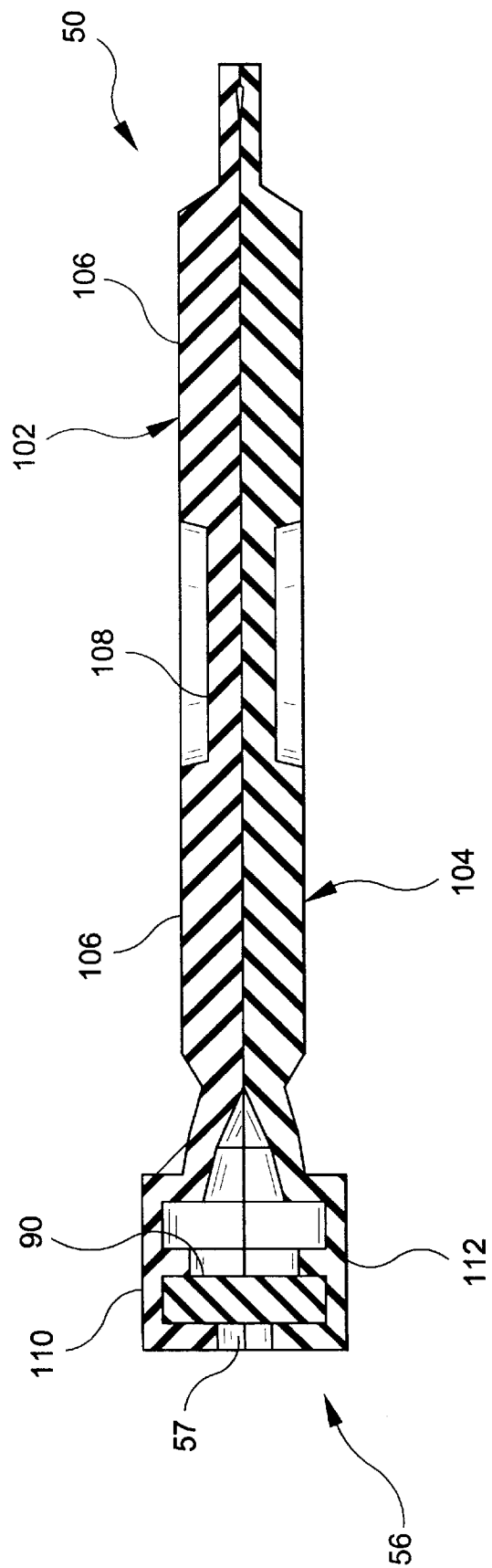

FIGS. 3 and 4 are exploded views which illustrate the internal components of the automatic injection device 20. These components include a liquid reservoir or dose chamber 50, a needle carrier 52 and an injection needle 54. The liquid reservoir 50, whose detailed construction will be discussed below in connection with FIGS. 9–11, is preferably in the form of a thin disk-shaped structure as shown. A cylindrical fill and discharge port 56 is formed on the side of the reservoir 50 and faces the rear edge 69 of the needle carrier 52. The liquid reservoir 50 is made of a suitable plastic material, such as ABS plastic, and defines a thin, disk-shaped internal chamber in which a liquid therapeutic preparation (such as insulin) is stored. The circular aperture 57 of the port 56 is closed off by an internal, self-sealing rubber septum (not visible in FIGS. 3 and 4) which maintains the reservoir 50 in a sealed condition until it is penetrated by the injection needle 54 during use of the device 20. Preferably, the reservoir 50 is pre-filled with the liquid therapeutic preparation (via needle injection through the port 56) and is inserted into the automatic injection device 20 through the slot 32 after the device 20 has been assembled. When the reservoir 50 is inserted into the slot 32, a pair of upstanding ramps 58 which are integrally formed on the bottom portion 28 of the housing assist in locating the reservoir 50 at the proper height within the housing. A similar pair of ramps 60, spaced more closely together and located closer to the forward end 28 of the housing than the ramps 58, engage a pair of horizontal wings or tabs 62 which extend from either side of the port 56. As a result, the circular aperture 57 at the center of the port 56 is aligned precisely with the rearwardly-facing end 63 of the injection needle 54. When the reservoir 50 reaches the proper position within the housing 21, the rear edges of the wings 62 are captured between a pair of upstanding detents 64 which, like the ramps 58 and 60, are formed integrally with the bottom portion 24 of the housing 21. The detents 64 serve to lock the reservoir 50 in position within the housing 21 of the automatic injection device 20. The reservoir 50 is guided into engagement with the detents 64 by a shallow channel 65 which receives the lowermost edge of the port 56 and extends longitudinally along the interior surface of the bottom housing portion 24. A similar channel 66 extends longitudinally along the interior surface of the upper housing portion 22 to receive and guide the uppermost edge of the port 56.

With continued reference to FIGS. 3 and 4, the needle carrier 52 is received in the lower portion 24 of the housing in a side-by-side relationship with the reservoir 50. The needle carrier 52 is made of a strip of resilient plastic material, such as 0.040 inch thick ABS plastic. The needle carrier 52 includes a generally rectangular guide portion 68 on which the slide button 42 is integrally formed. The rear edge 69 of the guide portion 68 faces the reservoir 50, and is separated from the port 56 of the reservoir by a small gap 70 as shown in FIG. 3. Integral with the guide portion 68 of the needle carrier 52 is a resiliently deflectable portion 71 which, when viewed from above, has an arcuate or curved shape corresponding generally to the shape of the forward portion 28 of the housing. As best seen in FIG. 4, the resiliently deflectable portion 71 of the needle carrier 52 is angled downwardly (preferably by about 7°) from the plane of the guide portion 68 when the deflectable portion 71 is in its relaxed or unstressed condition. The injection needle 54 is secured to the bottom surface of the needle carrier 52 in a manner such that the main or unbent portion 72 of the injection needle 54 extends approximately parallel to the plane of the lower housing portion 24 and is aligned with the longitudinal center line of the device 20. The injection needle 54 may be affixed to the lower surface of the needle carrier 52 in any desired manner, but the preferred method is to capture portions of the injection needle 54 between projections (two of which are visible at 74 in FIG. 4) extending from the lower surface of the needle carrier 52. An epoxy resin may also be used to secure the injection needle 54 in place. The forward or distal end 76 of the injection needle 54 is bent at an angle of about 90° relative to the main or proximal portion 72 of the injection needle, and penetrates the skin of the patient during operation of the device 20. As described below in connection with FIGS. 7 and 8, the injection needle 54 is preferably made up of two connected sections of hollow 30-gauge stainless steel cannula, with each section ground at an angle at its free end to provide a sharpened distal end 78 and a sharpened proximal end 63. The 90° bend which separates the distal portion 76 of the injection needle 54 from the main or proximal portion 72 is preferably in the form of a smooth arc, as shown, in order to avoid any obstruction in the flow of the liquid therapeutic preparation through the injection needle 54.

Unlike the liquid reservoir 50, which is held at a fixed position within the housing 21, the needle carrier 52 is slidable relative to the lower portion 24 of the housing. This is achieved by means of a pair of upstanding guide track structures 82 which are formed integrally with the lower portion 24 of the housing. As best seen in FIG. 3, the rectangular guide portion 68 of the needle carrier 52 is slidably received between the guide tracks 82 so that it can move longitudinally (i.e., in the direction toward the liquid reservoir 50) when the slide button 42 is manipulated by the user. This provides a corresponding motion of the injection needle 54, which is affixed to the bottom of the needle carrier 52 as described previously. During movement of the needle carrier 52, the upper and lower horizontal portions of the guide tracks 82 restrain vertical movement of the guide portion 68. When the needle carrier 52 is at its forwardmost position in the lower housing portion 24, the front edge 85 of the resiliently deflectable portion 71 is deflected upwardly from its relaxed or unstressed configuration by a pair of upstanding rectangular supports or projections 84 which are formed integrally with the bottom portion 24 of the housing near its forward end 28. Since the guide portion 68 at the rear of the needle carrier 52 is prevented from moving upwardly by the guide tracks 82, the needle carrier 52 is thus maintained in a resiliently stressed condition with the forward edge of the resiliently deflectable portion 70 bearing downwardly on the supports 84. This is the condition in which the needle carrier 52 exists prior to use of the automatic injection device 20. When the device 20 is used, the needle carrier 52 is moved (via the slide button 42) in the direction toward the reservoir 50, thereby removing the forward edge 85 of the resiliently deflectable portion 70 from contact with the supports 84. This allows the resiliently deflectable portion 70 of the needle carrier 52 to deflect downwardly under its own inherent spring force. This motion provides the injection force that causes the distal portion 76 of the injection needle 54 to penetrate the skin of the patient.

As shown in FIGS. 3 and 4, upstanding cylindrical sockets 86 are integrally formed on the interior surface of the lower housing portion 24. These sockets 86 mate with corresponding pins or studs 88 which are formed integrally with the interior surface of the upper housing portion 22 and which extend downwardly toward the lower housing portion. Tight engagement between the pins 88 and sockets 86 serves to couple the upper and lower housing portions 22 and 24 together during assembly of the automatic injection device 20.

Figure 5:
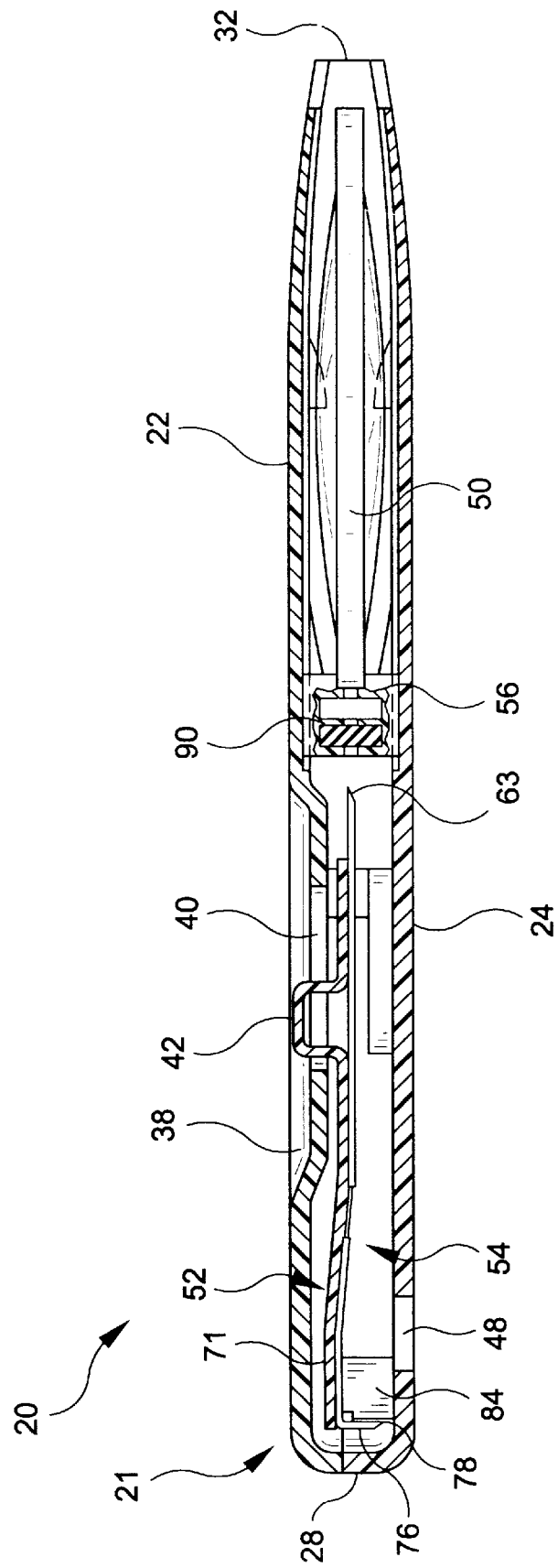
FIG. 5 is a cross-sectional view taken along the line 5—5 in FIG. 1, illustrating the components of the automatic injection device in the positions they occupy prior to use of the device.
Figure 6:
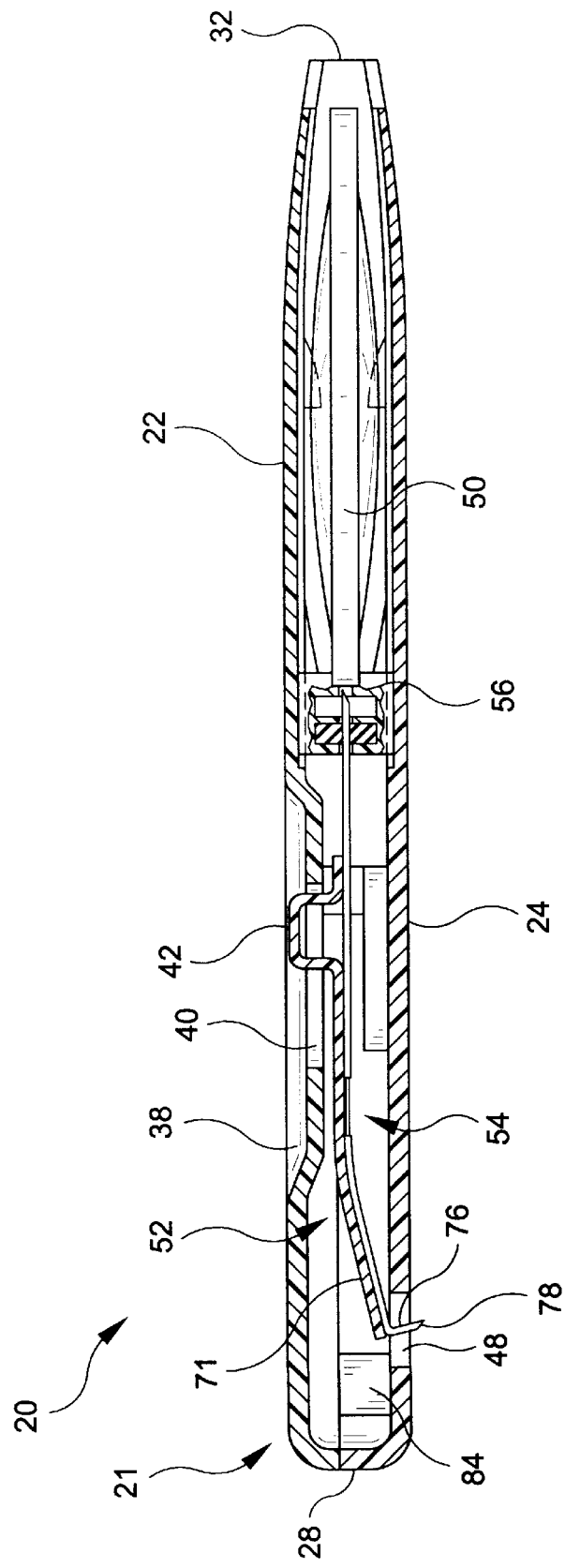
FIG. 6 is a cross-sectional view similar to that of FIG. 5, illustrating the components of the automatic injection device in the positions they occupy during and after use.

FIGS. 5 and 6 are cross-sectional views which illustrate the manner in which the automatic injection device 20 is used. FIG. 5 illustrates the device 20 as it would appear prior to use, with the slide button 42 in its forwardmost position and the distal tip 78 of the injection needle 54 recessed within the forward end 28 of the housing 21. The release liner 46 has been removed from the bottom of the housing 21 in FIG. 5, and the bottom surface of the housing has been placed against the skin of the patient (not shown) so that the needle aperture 48 is directly over the desired injection site. When the slide button 42 is moved rearwardly in the hole 40 (i.e., in the direction toward the reservoir 50), the forward edge 85 of the deflectable portion 71 of the needle carrier 52 is withdrawn from the supports 84, allowing the deflectable portion 71 to resiliently return to its relaxed or unstressed condition as shown in FIG. 6. When this occurs, the bent portion 76 of the injection needle 54 projects downwardly through the needle aperture 48 and the sharpened distal tip 78 of the injection needle penetrates the skin of the patient. The depth of penetration is preferably about 3 millimeters or less. At the same time, the rearward movement of the needle carrier 52 causes the sharpened tip 63 at the proximal end of the injection needle 54 to penetrate a self-sealing rubber septum 90 in the port 56 of the liquid reservoir 50. The proximal end of the injection needle 54 thereby enters the liquid chamber within the reservoir 50, as shown in FIG. 6, and a flow path is established between the reservoir 50 and the body of the patient through the lumen of the injection needle 54. It will be appreciated that contact between the port 56 and the read edge 69 of the needle carrier 52 will act as a stop for the rearward motion of the injection needle 54, thereby limiting the depth of penetration of the injection needle 54 into the reservoir 50. As will be discussed in connection with FIGS. 7 and 8, the rate of liquid flow through the injection needle 54 is controlled so that the liquid therapeutic preparation is discharged from the reservoir 50 gradually over a predetermined interval. In the case where the liquid therapeutic preparation is insulin, for example, this period of time may be approximately twenty-four hours. As will become apparent from the discussion of FIGS. 9–11 below, the inherent resiliency of the walls of the liquid reservoir 50 allows the liquid therapeutic preparation to be discharged from the reservoir 50 without the need for a pump or other type of discharge device.

Figure 7:
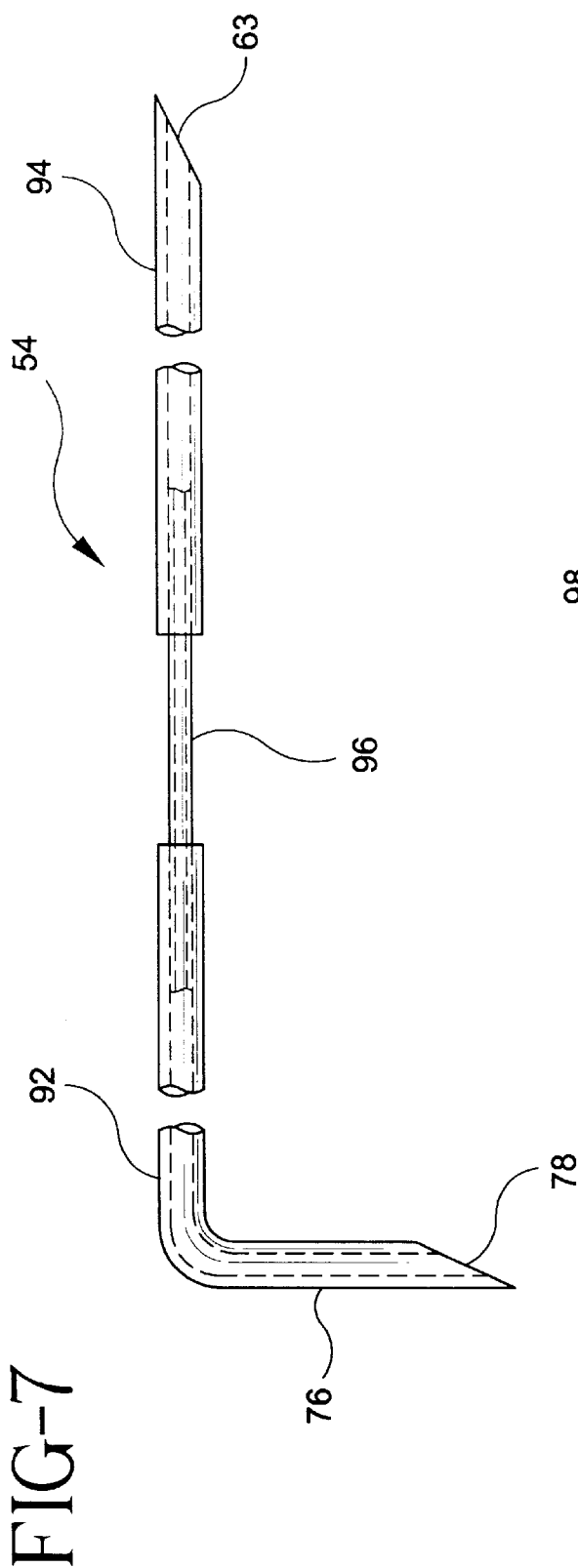
FIG. 7 is an enlarged side view of the injection needle used in the device of FIGS. 1–6, showing the capillary tube that is used for flow rate control.

FIG. 7 illustrates a preferred type of injection needle 54 which may be employed in the present invention. The injection needle 54 is made up of two sections 92 and 94, each consisting of a length of 30-gauge stainless steel cannula. A glass capillary tube is tightly received in the lumens of the cannula sections 92 and 94 and serves to couple them together. The length and inner diameter of the glass capillary tube 96 provides a fixed, calibrated flow resistance that establishes the rate of liquid flow through the injection needle 54. In the preferred embodiment, the glass capillary tube 96 has a length of approximately 1 inch, an outer diameter of approximately 150 microns and an inner diameter of approximately 29 microns. The epoxy resin that is used to attach the injection needle 54 to the needle carrier 52 may also be used to secure the connection between the glass capillary tube 96 and the stainless steel cannula sections 92 and 94.

Figure 8:
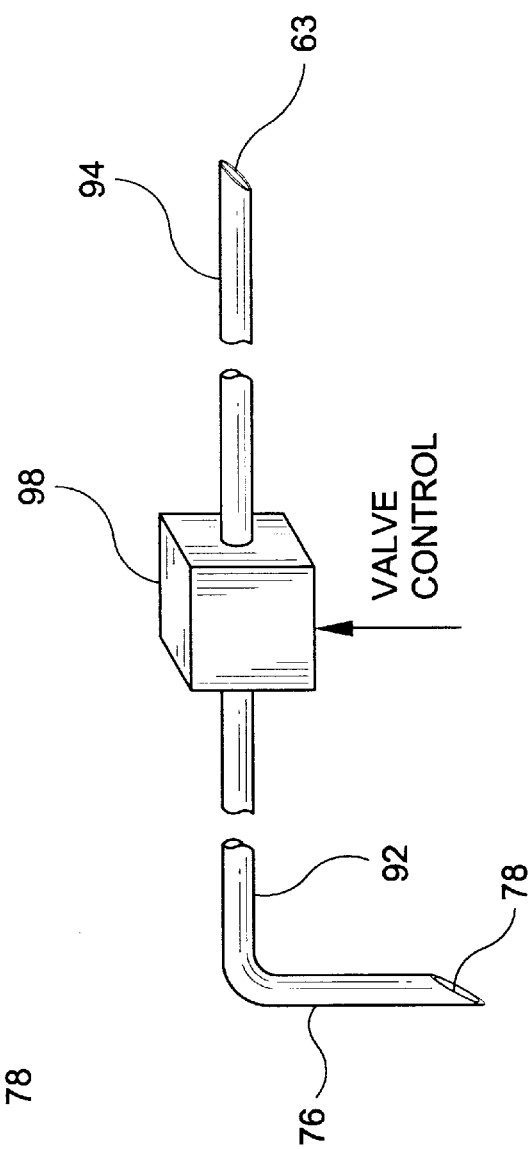
FIG. 8 is a side view of an alternative embodiment of the injection needle in which a valve is used for flow rate control.

FIG. 8 illustrates a modified embodiment in which the cannula sections 92 and 94 are coupled by a valve 98 rather than by the glass capillary tube 96. When the valve 98 is closed, the liquid therapeutic preparation is prevented from flowing through the injection needle 54. When the valve 98 is opened, the liquid therapeutic preparation can flow through the injection needle 54 and into the body of the patient. The size of the valve orifice controls the rate of liquid flow through the injection needle 54. The valve 98 may be controlled either mechanically or electrically. In either case, the valve control can be interconnected with the slide button 42 or provided as a separate control on the exterior of the housing 21. Optionally, a proportional valve may be used so that the rate of liquid flow through the injection needle 54 can be varied to suit the requirements of particular patients and/or liquid therapeutic preparations.

FIGS. 9–11 illustrate the details of the liquid reservoir 50. In FIG. 9, the reservoir 50 is shown in its assembled condition and is filled with a liquid therapeutic preparation 100. The body of the reservoir 50 consists of two circular Belleville spring diaphragms 102 and 104 which are bonded to each other at their edges. Each Belleville spring diaphragm is about 1.70 inches in diameter and is made of a suitable resilient plastic material, such as ABS or polycarbonate. Each Belleville spring diaphragm 102 and 104 includes an outer annular portion 106 which has a thickness of about 0.030 inch, and a thinner central disk portion 108 which has a thickness of about 0.020 inch. Semi-cylindrical structures 110 and 112 extend from one side of each Belleville spring diaphragm 102 and 104 to form the port 56. A self-sealing cylindrical rubber septum 90 is captured within a correspondingly-shaped cavity in the port 56 to seal the aperture 57, which serves as the inlet and outlet of the reservoir 50. In the empty condition of the reservoir 50, the inner surfaces of the Belleville spring diaphragms 102 and 104 are in contact with each other as shown in FIG. 11. The liquid therapeutic preparation 100 is injected under pressure by a filling needle through the rubber septum 90, and this causes the Belleville spring diaphragms 102 and 104 to forcibly separate as shown in FIG. 9. When the filling needle is removed, the rubber septum 90 self-seals and maintains the liquid therapeutic preparation 100 in a pressurized condition within the reservoir 50.

FIG. 10 illustrates the configuration of the Belleville spring diaphragms 102 and 104 before the reservoir 50 is assembled. As illustrated, each Belleville spring diaphragm 102 and 104 has the shape of a truncated cone, with the apexes of the two truncated cones facing each other. During the assembly process, the outer edges of the two Belleville spring diaphragms 102 and 104 are forced together and are secured to each other by ultrasonic welding. The ultrasonic welding process bonds the edges of the two Belleville spring diaphragms 102 and 104 together at all points along their peripheries, except for a gap in the region of the port 56. The gap provides a liquid channel which communicates with the septum 90 and aperture 57. After the ultrasonic bonding operation is complete, the reservoir 50 has the configuration shown in FIG. 11. As noted earlier, introduction of the liquid therapeutic preparation 100 under pressure through the septum 90 causes the Belleville spring diaphragms 102 and 104 to separate, leaving the reservoir in the condition shown in FIG. 9. The resiliency of the Belleville spring diaphragms 102 and 104 (which tends to return them to the configuration shown in FIG. 10) maintains the liquid therapeutic preparation 100 under pressure. When the injection needle 54 of the automatic injection device 20 penetrates the septum 90, the pressure exerted by the Belleville spring diaphragms 102 and 104 causes the liquid therapeutic preparation 100 to be discharged through the injection needle 54 without the need for a pump or other type of discharge device.

One of the advantages of the reservoir construction shown in FIGS. 9–11 is that the Belleville spring diaphragms 102 and 104 exert a relatively constant pressure on the liquid therapeutic preparation 100 that is essentially independent of the amount of liquid remaining within the reservoir 50. This produces a relatively constant flow rate of the liquid therapeutic preparation 100 through the injection needle 54, which allows the liquid therapeutic preparation 100 to be administered to the patient at a constant infusion rate. In order to achieve this result, a specific geometry is preferably used for each of the Belleville spring diaphragms 102 and 104. In particular, it has been found that the ratio between the vertical height projection of the thicker annular region 106 of each Belleville spring diaphragm (the dimension "h" in FIG. 10) and the thickness of this region (the dimension "t" in FIG. 10) should be in the range of about 1.7 to about 2.0. For a Belleville spring diaphragm having an effective diameter (the dimension "d" in FIG. 10) of about 1.70 inches, the dimension "h" preferably has a value of about 0.060 inch and the dimension "t" preferably has a value of about 0.030 inch. When the reservoir 50 is completely filled with the liquid therapeutic preparation as shown in FIG. 9, the interior height dimension at the center of the reservoir is about 0.060 inch.

Figure 12:
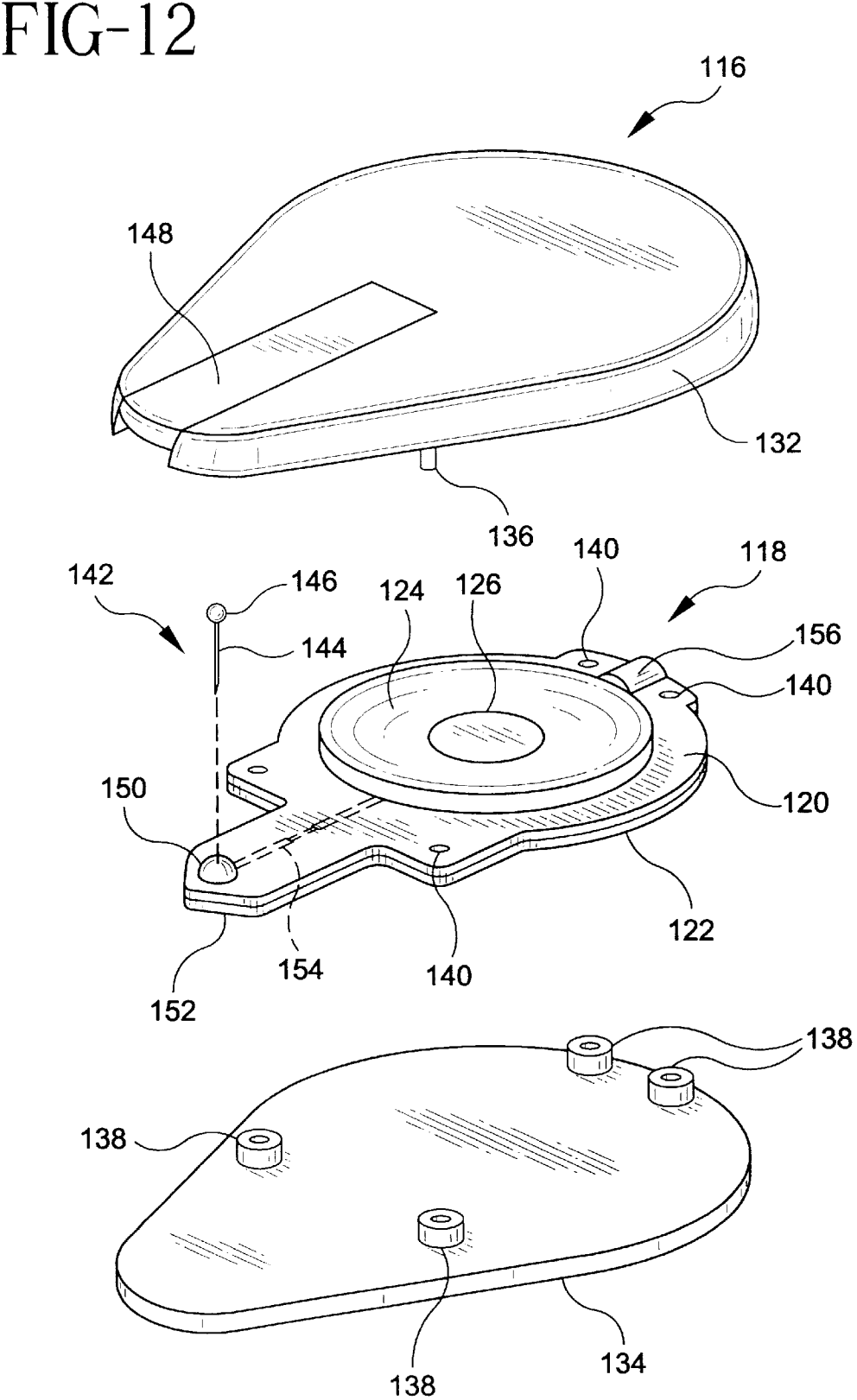
FIG. 12 is an exploded perspective view of an automatic injection device constructed in accordance with a second embodiment of the present invention.

FIG. 12 is an exploded perspective view of an automatic injection device 116 constructed in accordance with a second embodiment of the present invention. In this embodiment, the liquid reservoir 118 comprises two flexible membranes 120 and 122, made of rubber or plastic, which are bonded together at their outer edges. A Belleville washer 124 with a hollow center 126 is bonded to the outside of the top membrane 120, and a similar Belleville washer 128 (visible in FIG. 13) with a hollow center 130 is bonded to the outside of the bottom membrane 122. Except for their hollow centers 126 and 130, the Belleville washers 124 and 128 are similar in construction and function to the Belleville spring diaphragms 102 and 104 shown in FIGS. 9–11. In the embodiment of FIG. 12, however, the sole function of the Belleville washers 124 and 128 is to pressurize the liquid therapeutic preparation contained within the liquid reservoir 118, but the Belleville washers 124 and 128 do not themselves form the walls of the chamber. The latter function is carried out by the bonded membranes 120 and 122. This is advantageous in allowing the material of the Belleville washers 124 and 128 to be selected solely on the basis of its mechanical characteristics, without regard to its compatibility with the liquid therapeutic preparation contained in the reservoir 118.

With further reference to FIG. 12, the liquid reservoir 118 is enclosed in a housing which consists of an upper portion 132 and a lower portion 134. Pins 136 extend downwardly from the upper portion 132 of the housing and mate with sockets 138 formed in the lower portion 134 of the housing after passing through holes 140 located at the periphery of the bonded membranes 120 and 122. This method of construction serves to couple the upper and lower housing portions 132 and 134 together while properly locating the liquid reservoir 118 within the housing. Also visible in FIG. 12 is an injection needle 142 which communicates with the liquid reservoir 118. The injection needle 142 consists of a straight stainless steel cannula 144 which is ground at an angle at its lower end, and is capped at its upper end by a round plastic insert 146. Actuation of a hinged cut-out section 148 of the upper housing portion 132 by the user causes the injection needle to be displaced through a delivery node 150 formed in an extension 152 of the liquid reservoir 118. The delivery node 150 is in fluid communication with the liquid therapeutic preparation in the reservoir 118 by means of a glass capillary tube 154 which serves as a fixed flow resistor and establishes the desired flow rate of the liquid therapeutic preparation through the injection needle 142.

Figure 13:
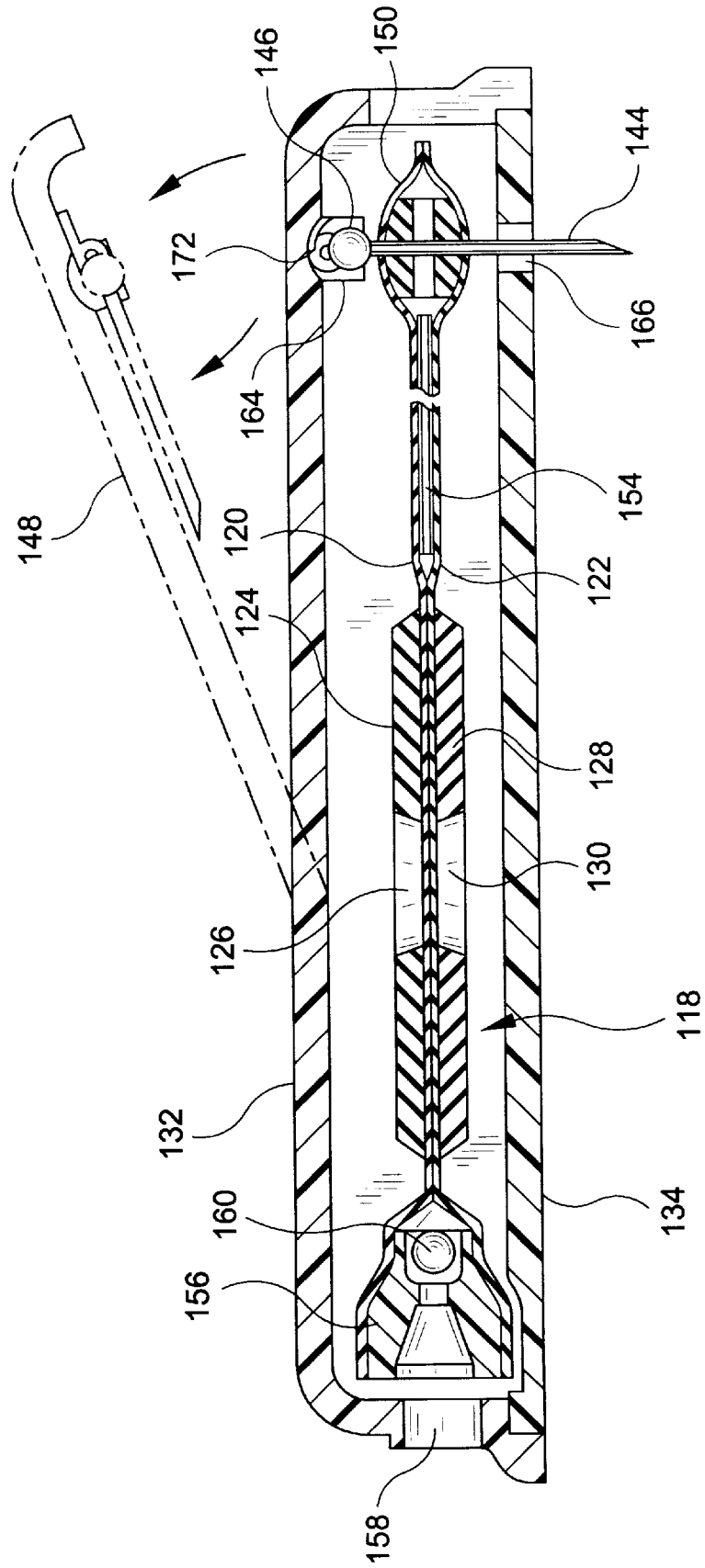
FIG. 13 is a cross-sectional view of the automatic injection device of FIG. 12, shown fully assembled.
Figure 14:
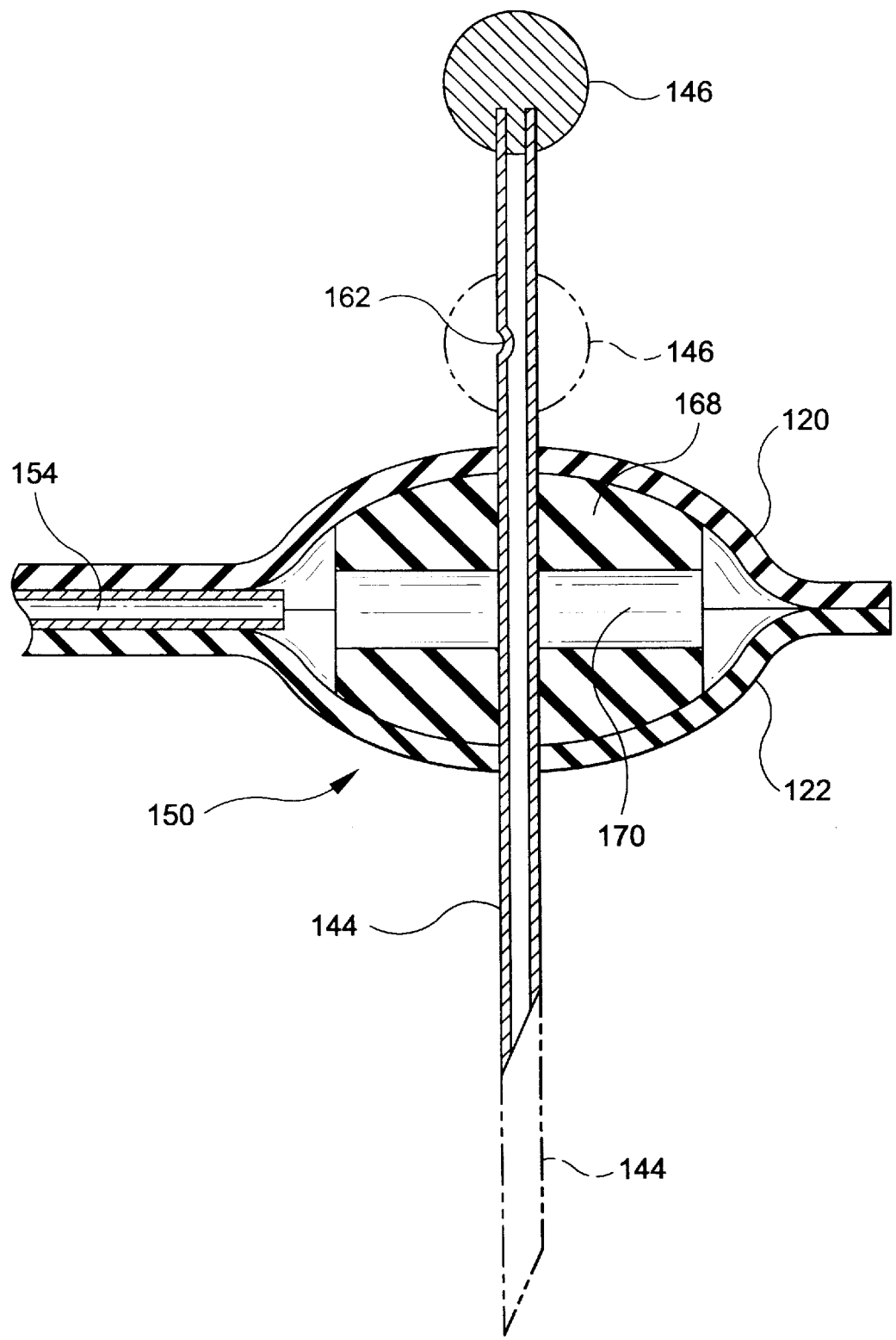
FIG. 14 is an enlarged view of a portion of FIG. 13, illustrating the manner in which the flow of the drug solution to the injection needle is controlled.

The manner in which the automatic injection device 116 of FIG. 13 is used will now be explained with reference to FIGS. 13 and 14. After the device 116 is assembled, the liquid reservoir 118 is filled by inserting a suitable filling nozzle through a hole 158 formed in the upper portion 132 of the housing and coupling the filling nozzle to a port 156 located on the rear portion of the reservoir 118. A ball-type check valve 160 allows the liquid therapeutic preparation to enter the reservoir 118 but prevents it from being discharged through the port 156 after the reservoir has been filled. Filling of the reservoir 118 will cause the membranes 120 and 122 and the Belleville washers 124 and 128 to forcibly separate, thereby defining a liquid chamber between the separated membranes and Belleville washers. Prior to use of the device 116, the movable section 148 of the upper housing portion 132 is in the portion shown in solid lines in FIG. 14. In this position, the cannula 144 of the injection needle 142 is recessed entirely within the housing, and a hole 162 formed in the side of the cannula 144 is located at a position above and outside the delivery node 150. As shown in FIG. 13, the plastic cap 146 at the top of the injection needle 142 is held in a socket 164 which is affixed to the bottom surface of the movable housing section 148. To inject the needle 142, the user depresses the movable housing section 148 until it reaches the solid line position shown in FIG. 13. This causes the distal end of the injection needle 142 to project from a needle aperture 166 in the bottom portion 134 of the housing, and also causes the portion of the injection needle cannula containing the hole 162 to enter the delivery node 150 (as illustrated in phantom lines in FIG. 14). When the hole 162 aligns with the center of the delivery node 150, a liquid path exists between the interior of the reservoir 118 and the distal tip of the injection needle 142. The liquid therapeutic preparation is then automatically discharged from the reservoir 118 through the injection needle 142 in the same manner as in the previous embodiment, with the rate of discharge being established by the dimensions of the glass capillary tube 154. An elastomeric seal 168 is provided in the delivery node 150 in order to prevent leakage of the liquid therapeutic preparation at the membranes 120, 122 and the cannula 144 of the injection needle 142. The elastomeric seal 168 also defines a central opening 170 with which the side opening 162 in the needle cannula 144 can align, thereby insuring that the desired fluid path will exist. The opening 162 can be formed in the cannula 144 in various ways, but a technique known as electrical discharge machining (EDM) is particularly useful for this purpose.

After the liquid therapeutic preparation has been completely discharged from the reservoir 118, the automatic injection device 116 can be removed from the body of the patient in the same manner as the device 20 described previously. At this point, the movable section 148 in the upper portion 132 of the housing can be raised to the position shown in phantom lines in FIG. 13. When this is done, the cannula 144 is withdrawn from the delivery node 150, and a spring 172 in the socket 164 causes the injection needle 142 to pivot to a position generally parallel to the inside surface of the movable housing section 148. The movable housing section 148 may then be restored to its closed position, leaving the injection needle 142 fully retracted at a safe position within the housing.

It will be appreciated that the automatic injection devices 20 and 116 can be used to administer virtually any type of therapeutic preparation that is in a liquid or flowable form. Examples include liquids, solutions, suspensions, flowable gels and the like. It will also be apparent that the devices 20 and 116 can be used for either intradermal, subcutaneous, intramuscular or intravenous delivery of the therapeutic preparation.

Although only two exemplary embodiments of the invention have been described in detail above, those skilled in the art will readily appreciate that many modifications are possible in the exemplary embodiments without materially departing from the novel teachings and advantages of this invention. Accordingly, all such modifications are intended to be included within the scope of the invention as defined in the following claims.

What is claimed is:

1. A device for containing and discharging a liquid preparation comprising:
    a) a reservoir comprising two Belleville spring diaphragms, wherein each Belleville spring diaphragm includes an outer annular portion and a central disk portion which is thinner than the outer annular portion and the Belleville spring diaphragms are bonded together at an outer edge of each Belleville spring diaphragm such that a liquid contained within the reservoir is maintained under pressure by the Belleville spring diaphragms;
    b) an aperture in the reservoir for allowing discharge of the liquid from the reservoir; and
    c) means for sealing the aperture until discharge of the liquid is desired.

2. The device of claim 1 wherein the Belleville spring diaphragms comprise ABS or plastic.

3. The device of claim 1 wherein the means for sealing the aperture is a self-sealing septum.

4. The device of claim 1 wherein the means for sealing the aperature is an elastomeric seal.

5. The device of claim 1 wherein the ratio of the vertical height of the annular portion of the Belleville spring diaphragm and the thickness of the annular portion of the Belleville spring diaphragm is between 1.7 and 2.0.

6. The device of claim 1 further comprising a port in the reservoir for allowing filling of the reservoir and means for sealing the port after filling the reservoir.

7. The device of claim 1 wherein the means for sealing the port is a ball-type check valve.

8. A device for containing and discharging a liquid preparation comprising:
    a) a reservoir comprising a first and a second flexible membrane bonded together at an outer edge of each membrane and a first Belleville washer bonded to the first flexible membrane and a second Belleville washer bonded to the second flexible membrane such that a liquid contained within the reservoir is maintained under pressure by the Belleville washers;
    b) an aperture in the reservoir for allowing discharge of the liquid from the reservoir; and
    c) means for sealing the aperture until discharge of the liquid is desired.

9. The device of claim 8 wherein the first and second flexible membranes are comprised of rubber or plastic.

10. The device of claim 8 wherein the Belleville washers are comprised of ABS or plastic.

11. The device of claim 8 wherein the means for sealing the aperture is a self-sealing septum.

12. The device of claim 8 wherein the means for sealing the aperature is an elastomeric seal.

13. The device of claim 8 wherein the ratio of the vertical height of the Belleville washer and the thickness of the Belleville washer is between 1.7 and 2.0.

14. The device of claim 8 further comprising a port in the reservoir for allowing filling of the reservoir and means for sealing the port after filling the reservoir.

15. The device of claim 8 wherein the means for sealing the port is a ball-type check valve.

16. A device for containing and discharging a liquid preparation comprising:
    (a) a reservoir comprising first and second Belleville means for pressurizing a liquid contained within the reservoir;
    (b) an aperture in the reservoir for allowing discharge of the liquid from the reservoir; and
    (c) means for sealing the aperture until discharge of the liquid is desired.

* * * * *